United States Patent [19]
Voorhees et al.

[11] Patent Number: 5,837,224
[45] Date of Patent: Nov. 17, 1998

[54] METHOD OF INHIBITING PHOTOAGING OF SKIN

[75] Inventors: John J. Voorhees, Ann Arbor; Gary J. Fisher, Ypsilanti, both of Mich.

[73] Assignee: The Regents of the University of Michigan, Ann Arbor, Mich.

[21] Appl. No.: 588,771

[22] Filed: Jan. 19, 1996

[51] Int. Cl.$^6$ .............................. A61K 7/42; A61K 31/59
[52] U.S. Cl. ................... 424/59; 424/60; 514/167
[58] Field of Search ..................... 424/59, 60; 514/167

[56] References Cited

U.S. PATENT DOCUMENTS

| | | | |
|---|---|---|---|
| 4,603,146 | 7/1986 | Kligman | 514/559 |
| 4,877,805 | 10/1989 | Kligman | 514/381 |
| 4,994,491 | 2/1991 | Purcell et al. | 514/529 |
| 5,019,569 | 5/1991 | Kligman et al. | 514/171 |
| 5,051,449 | 9/1991 | Kligman | 514/559 |

FOREIGN PATENT DOCUMENTS

| | | |
|---|---|---|
| 0379367 | 7/1990 | European Pat. Off. . |
| 0586106 | 3/1994 | European Pat. Off. . |
| WO 88/07857 | 10/1988 | WIPO . |

OTHER PUBLICATIONS

Rieger, "Oxidative reactions in and on skin: Mechanism and prevention" *Cosmetics and Toiletries* (1993) 108:43–56.

Angel et al., "Phorbol ester–inducible genes contain a common Cis element recognized by a TPA–modulated trans–acting factor" *Cell* (1987) 49:729–739.

Sato et al., "Regulatory mechanism of 92 kDa type IV collagenase gene expression which is associated with invasiveness of tumor cells" *Oncogene* (1993) 8:395–405.

Devary et al., "NF–kB activation by ultraviolet light not dependent on a nuclear signal" *Science* (1993) 261:1442–1445.

Wlaschek et al., "UVA–induced autocrine stimulation of fibroblast–derived collagenase/MMP–1 by interrelated loops of interleukin–1 and interleukin–6" *Photochemistry and Photobiology* (1994) 59(5):550–556.

Hill et al., "Inhibition of bone resorption in vitro by selective injibitors of gelatinase and collagenase" *Biochem. J.* (1995) 308:167–175.

Gowravaram et al., "Inhibition of matrix metalloproteinases by hydroxylamates containing heteroatom–based modification of the $P_1$' group" *J. Med. Chem.* (1995) 38:2570–2581.

Hodgson, "Remodeling MMPIs" *Biotechnology* (1995) 13:554–557.

Conway et al., "Inhibition of cartilage and bone destruction in adjuvant arthritis in the rate by a matirx metalloproteinase inhibitor" *J. Exp. Med.* (1995) 182:449–457.

Mauch et al., "Role of the extracellular matrix in the degradation of connective tissue" *Arch. Dermatol. Res.* (1994) 287:107–114.

Fanjul et al., "A new class of retinoids with selective inhibition of AP–1 inhibits proliferation" *Nature* (1994) 372:107–111.

Nicholson et al., "Negative regulation of the rat stomelysin gene promoter by retinoic acid is mediated by an AP1 binding site" *EMBO Journal* (1990) 9(13):4443–4454.

Bailly et al., "Retinoic acid inhibits the production of collagenase by human epidermal keratinocytes" *J. Investig. Derm.* (1990) 94(1):47–51.

Fujimori et al., "A new anti–platelet drug, E5510, has multiple suppressive sites during receptor–mediated signal transduction in human platelets" *Japan. J. Pharmacol.* (1991) 55(1):81–91.

Garcia et al., "Peptidomimetic inhibitors of Ras farnesylation and function in whole cells" *J. Biol. Chem.* (1993) 268(25):18415–18418.

Dalton et al., "The farnesy protein transferase inhibitor BZA–5B blocks farnesylation of nuclear lamins and $p21^{ras}$ but does not affect their function or localization" *Cancer Res.* (1995) 55(15):3295–3304.

Lee et al., "A protein kinase involved in the regulation of inflammatory cytokine biosynthesis" *Nature* (1994) 372:739–746.

Dudley et al., "A synthetic inhibitor of the mitogen–activated protein kinase cascade" *Proc. Natl. Acad. Sci. USA* (1995) 92:7686–7689.

Gearing et al., "Processing of human tumor necrosis factor–α precursor by metalloproteinases" *Nature* (1994) 370:555–557.

McGeehan et al., "Regulation of tumor necrosis factor–α processing by a metalloproteinase inhibitor" *Nature* (1994) 370:558–561.

Fisher et al., "Cellular, immunologic and bochemical characterization of topical retinoic acid–treated human skin" *J. Investig. Derm.* (1991) 96:699–707.

Hu et al., "A new assay for collagenolytic activity" *Anal. Biochem.* (1978) 88:638–643.

Hibbs et al., "Biochemical and immunological characterization of the secreted forms of human neutrophil gelatinase" *J. Biol. Chem.* (1985) 260:2493–2500.

Werb et al., "Signal transduction through the fibronectin receptor induces collagenase and stromelysin gene expression" *J. Cell Biol.* (1989) 109:877–889.

Murphy et al., "Characterization of gelatinase from pig polymorphonuclear leucocytes" *Biochem. J.* (1989) 258:463–472.

(List continued on next page.)

*Primary Examiner*—Shelley A. Dodson
*Attorney, Agent, or Firm*—Hopgood, Calimafde, Kalil & Judlowe LLP

[57] ABSTRACT

Photoaging of undamaged skin due to UVB irradiation exposure is inhibited by administering an agent that inhibits (1) the activity of UVB irradiation inducible MMPs in the skin, (2) one or both of the transcription factors AP-1 and NF-κB or (3) at least one of the GTP binding proteins or kinases involved in the activation and/or production of jun or fos proteins, which comprise AP-1, to the skin prior to such exposure.

20 Claims, 8 Drawing Sheets

OTHER PUBLICATIONS

Fisher et al., "Immunological identification and functional quantification of retinoic acid and retinoid X receptor proteins in human skin" *J. Biol. Chem.* (1994) 269:20629–20635.

Anderson et al., "Separation of oxidant–initiated and redox–regulated steps in the NF–kB signal transduction pathway" *Proc. Natl. Acad. Sci. USA* (1994) 91:11527–11531.

Angel et al., "Specific members of the Jun protein familiy regulate collagenase expression in response to various extracellular stimuli" *Matrix supp.* (1992) 1:156–164.

Applegate et al., "Cellular defense mechanisms of the skin against oxidant stress and in particular UVA radiation" *Eur. J. Dermatol.* (1995) 5:97–103.

Blundell, "Metalloproteins super–families and drug design" *Struc. Bio.* (1994) 1(2):73–75.

Brash et al., "Wrinkles waiting for $GOD_oT$" *Nature* (1996) 379:301–302.

Burke, "Facial wrinkles: Prevention and non–surgical correction" *Postgrad. Med.* (1990) 88(1):207–224.

Caldenhoven et al., "Negative cross–talk between RelA and the glucocorticoid receptor: a possible mechanism for the antiinflammatory action of glucocorticoids" *Mol. Endoc.*(1995) 9(4):401–412.

Carbonare et al., "Skin photosensitizing agents and the role of reactive oxygen species in photoaging" *J. Photochem. Photobiol.* (1992) 14:105–124.

Carboni et al., "Farnesyltransferase inhibitors are inhibitors of Ras but not R–Ras2/TC21, transformation" *Oncogene* (1995) 10:1905–1913.

Chen et al., "RAR–specific agonist/antagonists which dissociate transactivation and AP1 transrepression inhibit anchorage–independent cell proliferation" *EMBO Journal* (1995) 14(6):1187–1197.

Coso et al., "The small GTP–binding proteins Rac1 and Cdc42 regulate the activity of the JNK/SAPK signalling pathway" *Cell* (1995) 81:1137–1146.

Cowley, "Melatonin" *Newsweek* (1995) Aug. 7: 47–49.

Dérijard et al., "JNK1: A protein kinase stimulated by UV light and Ha–Ras that binds and phosphorylates the c–jun Activation Domain" *Cell* (1994) 76:1025–1037.

Devary et al., "Rapid and preferential acivation of the c–jun gene during the mammalian UV response" *Mol. Cell. Biol.* (1991) 11(5):2804–2811.

Devary et al., "The mammalian ultraviolet response is triggered by activation of Src tyrosine kinases" *Cell* (1992) 71:1081–1091.

Eisen, "Human skin collagenase: localization and distribution in normal human skin" *J. Invest. Derm.* (1969) 52(5):442–448.

Elias et al., (eds.), "Topical retinoids: An update" *J. Am. Acad. Dermatol.* Proceedings of a Symposium held Apr. 19–20, 1996, New York, N.Y., pp. 3A–5A.

Elmets et al., "Photoprotective effects of sunscreens in cosmetics on sunburn and Langerhans cell photodamage" *Photodermatol Photoimmunol Photomed.* (1992) 9:113–120.

Engelberg et al., "The UV response involving the Ras signalling pathway and AP–1 trascription factors is conserved between yeast and mammals" *Cell* (1994) 77:381–390.

Fisher et al., "Molecular basis of sun induced premature skin ageing and retinoid antagonism" *Nature* (1996) 379:335–339.

Frisch et al., "Positve and negative transcriptional elements of the human type IV collagenase gene" *Mol. Cell Biol.* (1990) 10(12):6524–6532.

Guercio–Hauer., "Photodamage, photoaging and photoprotection of the skin" *Amer. Fam. Phys.* (1994) 50(2):327, 330–332.

Jurkiewicz et al., "Effect of topically added applied tocopherol on ultraviolet radiation–mediated free radical damage in skin" *J. Invest. Dermatol.* (1995) 104(4):484–488.

Kaidbey et al., "Effects of intensive application of retinoic acid on human skin" *Brit. J. Dermatol.* (1975) 92:693–701.

Karin, Signal transduction from the cell surface to the nucleus through the phosphorylation of transcription factors *Current Opin. Cell Biol.* (1994) 6:415–424.

Karin, "The regulation of AP–1 activity by mitogen activated protein kinases" *J. Biol. Chem.* (1995) 270(28):16483–16486.

Kligman et al., "Enhanced repair of UV–induced dermal damage by topical retinoic acid" *Trends in Research and Therapy, Retinoid Symposium*, Saurat, (ed.) Geneva (1984) pp. 265–271.

Kligman et al., "Topical retinoic acid enhances the repair of ultraviolet damaged dermal connective tissue" *Connective Tiss. Res.* (1984) 12:139–150.

Kligman et al., "The nature of photoaging: Its prevention and repair" *Photodermatol.* (1986) 3:215–227.

Kligman et al., "Therapeutic aspects of retinoic acid in photoaging" *Sem. Dermatol.* (1987) 6(2):136–140.

Kligman, "Current status of topical tretinoin in the treatment of photoaged skin" *Drugs & Aging* (1992) 2(1):7–13.

Kligman, "Tretinoin (Retin–A) therapy of photoaged skin" *Comp. Therapy* (1992) 18(9):10–13.

Kligman et al., "Effects of topical treinoin on non–sun–exposed protected skin of the elderly" *J. Am. Acad. Dermatol.* (1993) 29:25–33.

Kligman et al., "Histological changes in facial skin after daily application of tretinoin for 5 to 6 years" *J. Dermatol. Treat.* (1993) 4:113–117.

Kligman et al., "Treatment of Photoaged skin with topical treatment" *Skin Pharmacol.* (1993) 6:78–82.

Khokha et al., "Utilization of transgenic mice in the study pf matrix degrading proteinases and their inhibitors" *Cancer Metastasis Rev.* (1995) 14:97–111.

Lavker, "Structural alterations in exposed and unexposed aged skin" *J. Invest. Dermatol.* (1979) 73(1):59–66.

Livingstone et al., "ATF–2 contains a phosphorylation–dependent transcriptional activation domain" *EMBO Journal* (1995) 14(8):1785–1797.

Lowry et al., "Rational cancer therapy" *Nature Medicine* (1995) 1(8):747–748.

Lu et al., "Effect of curcumin on 12–o–tetradecanoylphorbol–13–acetate– and ultraviolet B light–induced expression of c–Jun and c–Fos in JB6 cells and in mouse epidermis" *Carcinogenesis* (1994) 15(10):2363–2370.

Minden et al., "Selective activation of the JNK signaling cascade and c–jun transcriptional activity by the small GTPases Rac and Cdc42Hs" *Cell* (1995) 81:1147–1157.

Nagpal et al., "Separation of transactivation and AP1 antagonism functions of retinoic acid receptor α" *J. Biol. Chem.* (1995) 270(2):923–927.

Nicol et al., "Photodamage: Cause, clinical manifestations, and prevention" *Dermatol. Nursing* (1993) 5(4):263–277.

Oikarinen et al., "Demonstration of 72–kDa and 92–KkDa forms of type IV collagenase in human skin: variable expression in various blistering diseases, induction during Reepithelialization, and decreases by topical glucocorticoids" *J. Invest. Derm.* (1993) 101(2):205–210.

Pfahl, "Nuclear Receptor/AP–1 interaction" *Endoc. Rev.* (1993) 14(5):651–658.

Quinones et al., "Promoter elements in the transcriptional activation of the human stromelysin–1 gene by the inflammatory cytokine, interleukin–1" *Biochem. J.* (1994) 302:471–477.

Rafal et al., "Topical tretinoin (retinoic acid) treatment for liver spots associated with photodamage" *New Engl. J. Medicine* (1992) 326(6):368–374.

Saarialho–Kere et al., "Distinct phosphorylations of basal keratinocytes express stromelysin–1 and stromelysin–2 in chronic wounds" *J. Clin. Invest.* (1994) 94:79–88.

Sachsenmaier et al., "Involvement of growth factor receptors in the mammalian UVC response" *Cell* (1994) 78:963–972.

Salbert et al., "Retinoic acid receptors amd retinoid x receptor–α down–regulate the transforming growth factor–β promoter by antagonizing AP–1 activity" *Mol. Endocrinol.* (1993) 7(10):1347–1356.

Savouré et al., "Vitamin A status and metabolism of cutaneous polyamines in the hairless mouse after UV irradiation: Action of β–carotene and astaxanthin" *Internat. J. Vit. Nutr. Res.* (1995) 65:79–86.

Schenk et al., "Distinct effects of thioredoxin and antioxidants on the activation of transcription factors NF–kB and APP–1" *Proc. Natl. Acad. Sci. USA* (1994) 91:1672–1676.

Schüle et al., "Functional antagonism between oncoprotein c–Jun and the glucocorticoid receptor" *Cell* (1990) 62:1217–1226.

Smith et al., "Alterations in human dermal connective tissue with age and chronic sun damsge" *J. Investig. Dermatol.* (1962) 39(1):347–349.

Suhaimi et al., "Circumin in a model skin lotion formulation" *J. Pharm. Sci.* (1995) 84(3):376380.

Talwar et al., "Reduced type I and type II procollagens in photodamaged adult human skin" *J. Invest. Dermatol.* (1995) 105(2):285–290.

Taylor et al., "Photoaging/photodamage and photoprotection" *J. Amer. Acad. Derm.* (1990) 22:1–15.

Uitto et al., "Doxycyline and chemically modified tetracyclines inhibit gelatinase A (MMP–2) gene expresion in human skin keratinocytes" *Ann. N.Y. Acad. Sci.* (1994) 732:140–151.

van Dam et al., "ATF–2 is preferentially activated by stress activated protein kinases to mediate c–jun induction in response to genotoxic agents" *EMBO Journal* (1995) 14(8):1798–1811.

van den Broeke et al., "The effect of N–acetylcysteine on the UVB–induced inhibition of epidermal DNA synthesis in rat skin" *J. Photochem. Photobiol.* (1994) 26:271–276.

Warren et al., "Age, sunlight, and facial skin: a histologic and quantitative study" *J. Am. Acad. Dermatol.* (1991) 25:751–760.

Weinstein et al., "Collagen and elastin of human dermis" *J. Invest. Dermatol.* (1960) 35:227–229.

Whitmarsh et al., "Integration of MAP kinase signal transduction pathways at the serum response element" *Science* (1995) 269:403–407.

Yang–Yen et al., "Transcriptional interference between c–Jun and the glucocorticoid receptor: mutual inhibition of DNA binding due to direct protein–protein interaction" *Cell* (1990) 62:1205–1215.

Yoshioka et al., "Antitumor promotion by phenolic antioxidants: Inhibition of AP–1 activity through induciton of Fra expression" *Proc. Natl. Acad. Sci. USA* (1995) 92:4972–4976.

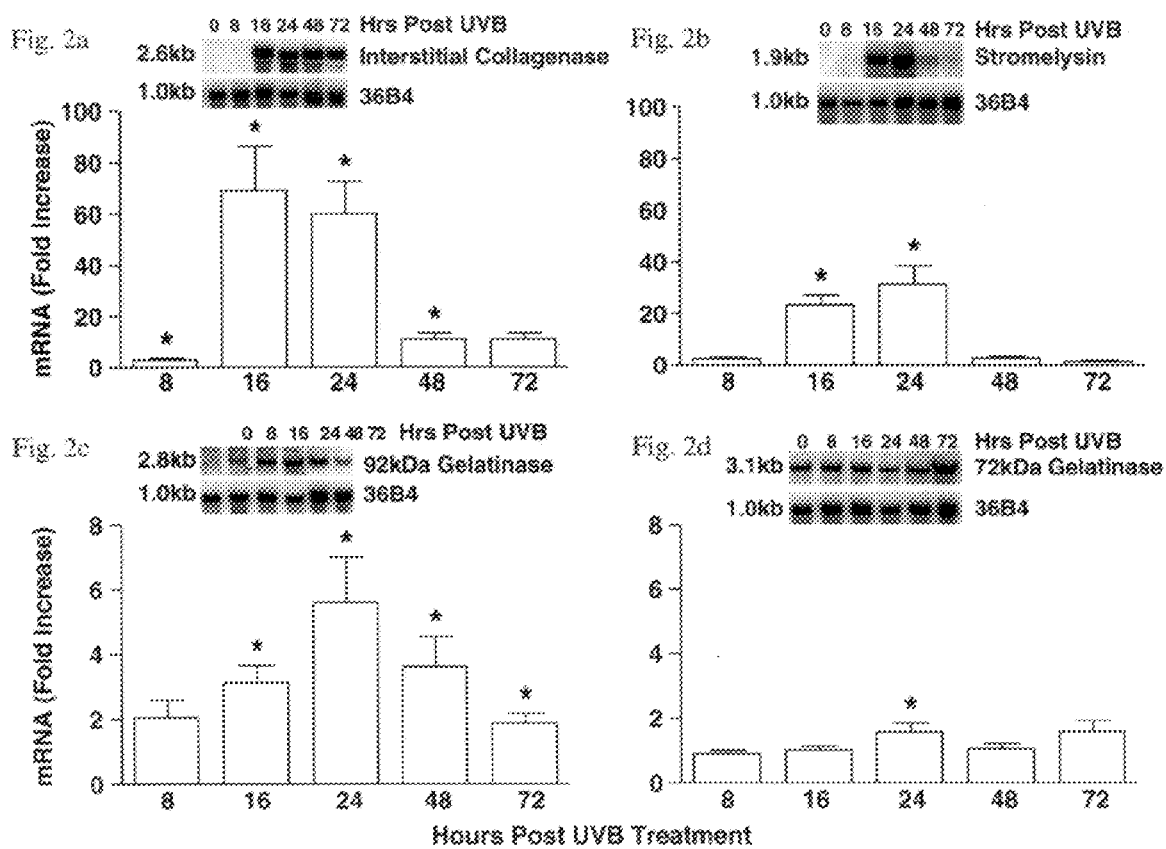

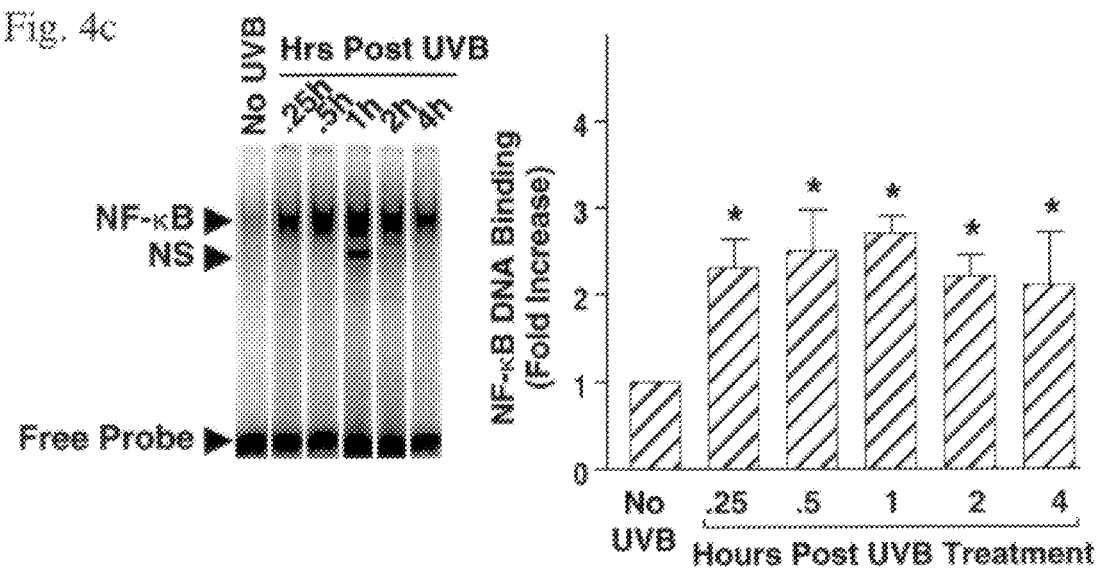
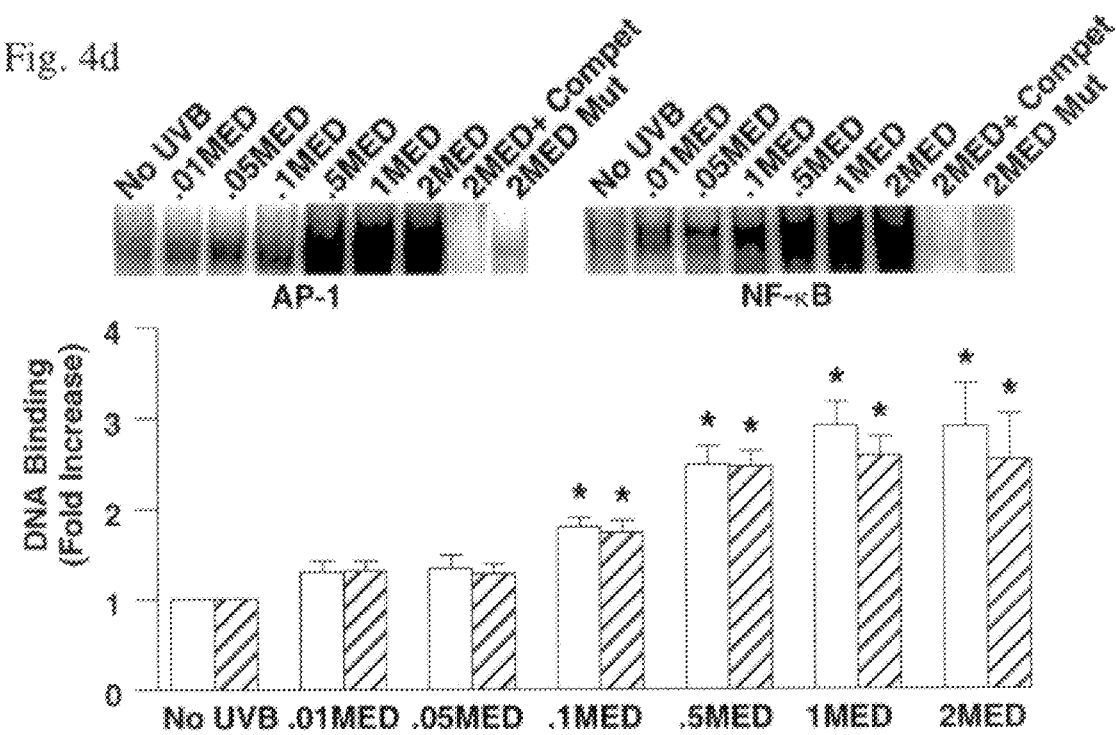

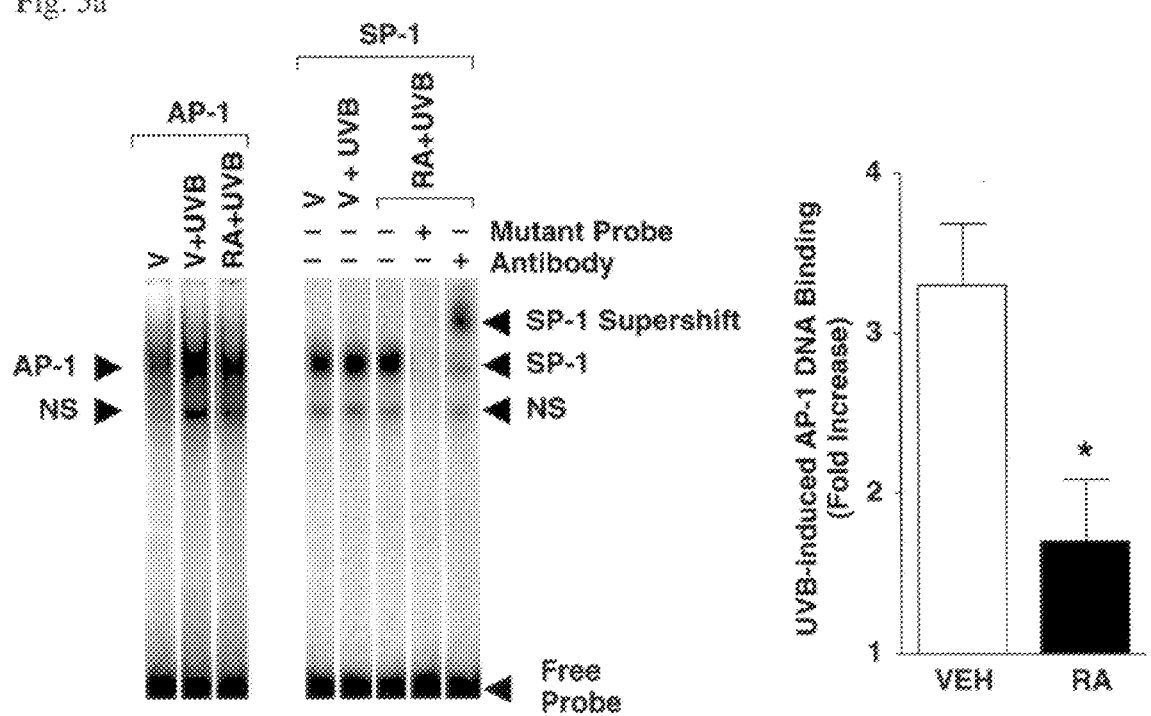

METHOD OF INHIBITING PHOTOAGING OF SKIN

TECHNICAL FIELD

This invention is in the field of photoprotection. More particularly it relates to a method for inhibiting photoaging of undamaged skin using inhibitors of matrix metalloproteinase (MMP) production and/or activity.

BACKGROUND

Photoaging is a term used to describe the changes in appearance and function of skin as a result of repeated exposure to sunlight. The ultraviolet (UV) component of sunlight, particularly middle UV (called UVB, 290–320 nm wavelength) is the principal causative agent of photoaging. The extent of UVB exposure required to cause photoaging is not currently known. Repeated exposure to UVB at levels that cause erythema and tanning are, however, commonly associated with photoaging. Clinically, photoaging is characterized by coarseness, wrinkling, mottled pigmentation, sallowness, laxity, telangiectasia, lentigines, purpura and easy bruising, atrophy, fibrotic depigmented areas, and ultimately premalignant and malignant neoplasms. Photoaging commonly occurs in skin that is habitually exposed to sunlight such as the face, ears, bald areas of the scalp, neck, and hands.

Procedures for preventing photoaging of unaged skin and treating already photoaged skin are available. Sunscreens are commonly used to prevent photoaging of skin areas that are habitually exposed to sunlight. Sunscreens are topical preparations that absorb, reflect or scatter UV. Some are based on opaque particulate materials such as zinc oxide, titanium oxide, clays and ferric chloride. Because such preparations are visible and occlusive many people consider these opaque formulations cosmetically unacceptable. Other sunscreens contain chemicals such a p-aminobenzoic acid (PABA), oxybenzone, dioxybenzone, ethylhexyl-methoxy cinnamide and butylmethoxydibenzoylmethane that are nonopaque and colorless because they do not absorb light of visible wavelengths. While these nonopaque sunscreens may be more acceptable cosmetically they are still relatively short-lived and susceptible to being removed by washing or perspiration. Additionally all sunscreens reduce vitamin D production.

Rieger, M. M. Cosmetics and Toiletries (1993) 108:43–56 reviews the role of reactive oxygen species (ROS) in UV-induced aging of skin. This article reports that topical application of known antioxidants to the skin can reduce the presence of ROS in the skin and thus reduce photodamage.

Retinoids have been used to retard the effects of photoaging in sun-damaged skin. U.S. Pat. No. 4,877,805 describes the treatment of photoaged skin as intervention therapy to decelerate the photoaging process. The patent indicates that there is little point in beginning such treatment until the effects of aging begin to appear. In this regard the present applicants know of no art that suggests the use of retinoids to prevent photoaging of undamaged skin.

MMPs are a family of enzymes that play a major role in physiological and pathological destruction of connective tissue. Over 10 members of the family have been identified. They are referred to numerically (MMP-1, MMP-2, etc.) as well as by common name. They appear to share several structural and functional properties but differ in their tissue substrate specificities. They include interstitial collagenase (MMP-1) and PMN-collagenase (MMP-8) that degrade collagen type I, II, III, VII, VIII, IX and gelatin; the 72 kDa (MMP-2) and 92kDa (MMP-9) type IV collagenases/gelatinases that degrade collagen types IV, V, VII, X, XI, gelatin, elastin, and fibronectin; stromelysin-1 (MMP-3), stromelysin-2 (MMP-10), and stromelysin-3 (MMP-11) that degrade fibronectin, PG core protein, collagen types IV, V, IX and X, laminin and elastin; PUMP-1 (MMP-7) that degrades collagen type IV, gelatin, laminin, fibronectin and PG core protein; and metalloelastase (MMP-12) that degrades elastin and fibronectin.

The expression of MMP genes is induced by the transcription factors AP-1 and NF-κB. Angel, P. et al., Cell (1987) 49:729–739 and Sato, H. and Seiki, M., Oncogene (1993) 8:395–405. AP-1 and NF-κB activities are mediated by cytokines (IL-I, IL-6, TNFα), growth factors TGFα, bFGF), and environmental stress such as oxidants, heat, and ultraviolet irradiation. AP-1 induction and production of jun proteins (C-jun, jun-B, and jun-D) and fos proteins (C-fos, fos-B, fra-1, and fra-2) that make up AP-1 are mediated by a host of molecules (e.g. RAC, CDC42, MEKK, JNKK, JNK, RAS, RAF, MEK, and ERK). It is known that AP-1 and NF-κB are activated in mammalian cells exposed to UV light. Devary, Y., et al. Science (1993) 261:1442–1445. Wlaschek, M. et al., Photochemistry and Photobiology (1994) 59(5):550–556 also report that UVA irradiation of fibroblasts resulted in an IL-1 and IL-6-mediated induction of MMP-1 and that such induction might contribute to the loss of collagen in photoaging.

Inhibitors of MMPs or the transcription factors that affect their expression are also known. Hill, P. A. et al., Biochem J (1995) 308: 167–175 describes two MMP inhibitors, CT1166 and RO317467. Gowravaram, M. R. et al., J Med Chem (1995) 38:2570–2581 describes the development of a series of hydroxamates that inhibit MMPs and mentions thiols, phosphonates, phosphinates, phosphoramidates and N-carboxy alkyls as known MMP inhibitors. This paper indicates that MMP inhibitors include a moiety that chelates zinc and a peptidic fragment that binds a subset of the specificity pockets of MMPs. Hodgson, J., Biotechnology (1995) 13:554–557 reviews the clinical status of several MMP inhibitors, including Galardin, Batimastat, and Marimastat. Other MMP inhibitors include butanediamide (Conway, J. G. et al., J Exp Med (1995) 182:449–457), TIMPs (Mauch C., et al., Arch Dermatol Res (1994) 287:107–114), and retinoids (Fanjul, A. et al., Nature (1994) 372:107–111; Nicholson, R. C. et al., EMBO Journal (1990) 9(13) 4443–4454; and Bailly, C. et al., J Investig Derm (1990) 94(1):47–51).

DISCLOSURE OF THE INVENTION

The present invention is based on applicants discovery that UVB exposure rapidly upgraded AP-1 and NF-κB in the exposed skin and led to MMP induction. The elevated levels of MMPs resulting from UVB degrade connective tissue proteins in skin. Such damage, if imperfectly repaired, results in solar scars which accumulate through repeated UVB exposure and cause photoaging.

Accordingly, applicants prevent photoaging of undamaged human skin due to exposure of the skin to UVB by administering an inhibitor of a UVB-inducible MMP to the human prior to said exposure in an amount sufficient to inhibit induction and/or activities of UVB-inducible MMPs. Surprisingly, this occurs at UVB doses below those that cause erythema as well as at those which cause erythema.

Another aspect of this invention is the use of an inhibitor of UVB-inducible MMP induction or activity in the manufacture of a medicament for preventing photoaging of undamaged skin due to repeated UVB exposure.

BRIEF DESCRIPTION OF THE DRAWINGS

In the drawings:

FIGS. 2a–d, 3a–b, 4a–d, and 5a–e are graphs of test results described in the Examples, infra.

MODES FOR CARRYING OUT THE INVENTION

The present invention is used to inhibit (i.e. reduce or prevent) photoaging of undamaged human skin, that is, skin that does not show the effects of photoaging. Treatment according to this invention should thus be practiced on skin such as that of the head, neck, hands and arms that in typical everyday living are habitually exposed to sunlight before such skin exhibits the telltale signs of photoaging. Because repeated exposure to doses of UVB below that which causes erythema can lead to photoaging, the invention should be practiced on skin subject to such low dose exposure. In this regard UVB doses in the range of 30–50 mJ/cm² skin cause erythema in most fair-skinned people. Accordingly the invention will prevent photoaging of skin subjected to doses below this range (typically above about 5 mJ/cm2 which is equivalent to a few minutes of sunlight exposure).

Photoaging is prevented or inhibited according to the invention by inhibiting UVB-induced degradation of the dermal extracellular matrix by MMPs. This is accomplished by administering a MMP inhibitor to the skin that is to be exposed to sunlight. In this regard the term "MMP inhibitor" intends those agents that directly or indirectly inhibit (i.e., reduce significantly or eliminate) the expression of UVB-inducible MMPs in such skin or inhibit the enzymatic activity of such MMPs. "Indirect inhibition" is intended to mean interaction with either or both of the transcription factors AP-1 and NF-κB and/or one or more of the molecules involved in the three kinase cascades that result in jun and fos protein induction in the skin in a manner that reduces or eliminates the expression of UVB-inducible MMPs.

Figure 1:
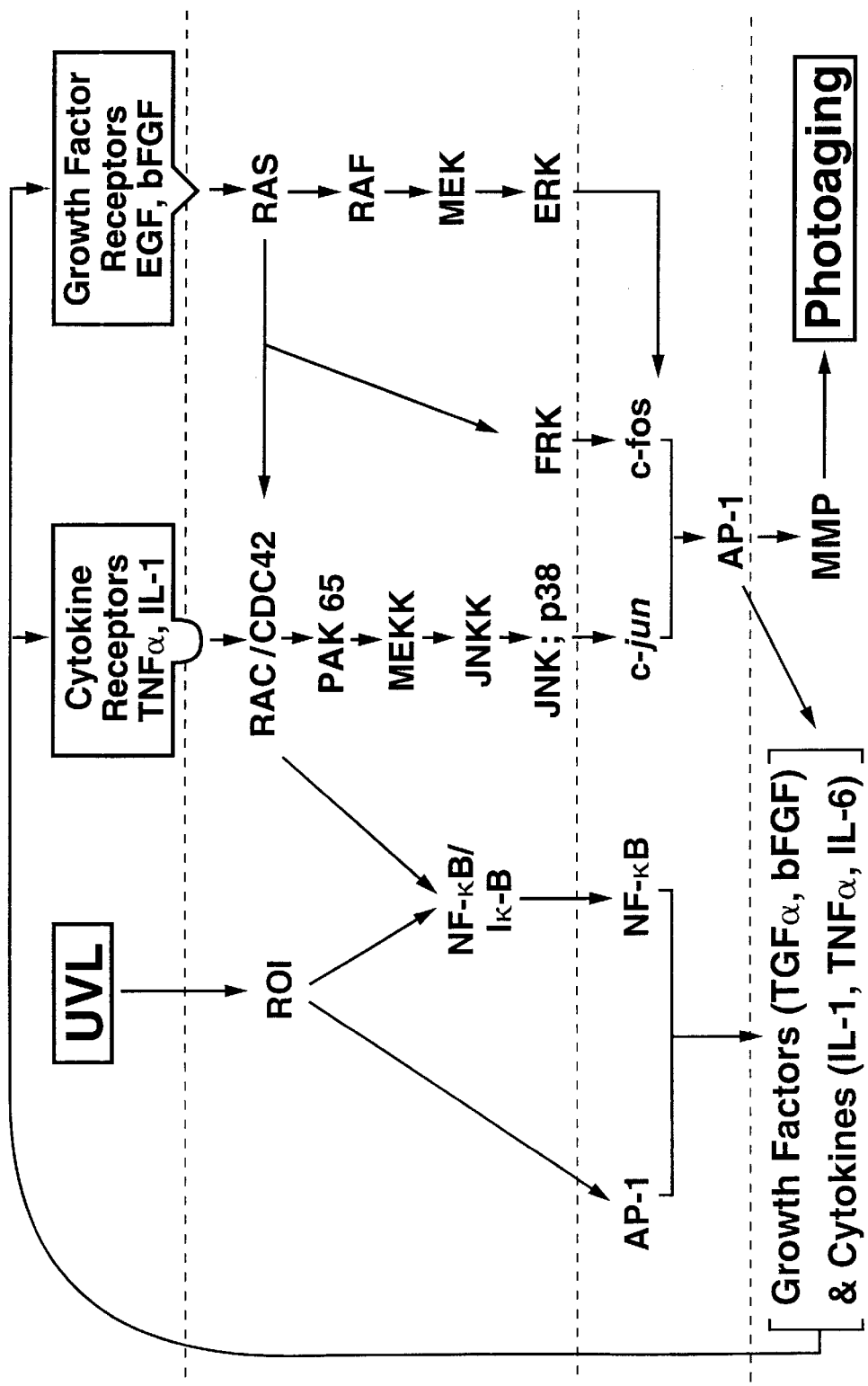
FIG. 1 is a flow chart showing the pathways by which UVB induces MMP production.

FIG. 1 schematically represents the pathways of UVB-inducible MMP expression. As shown in FIG. 1, UVB exposure generates reactive oxygen intermediates (ROI) which stimulate AP-1 and NF-κB activity which in turn induces cytokines and growth factors. The interaction of those cytokines and factors with their receptors trigger the small GTP binding proteins RAC/CDC42 and RAS. Those proteins activate the three kinase cascades that are essential to production of the jun and fos proteins which make-up AP-1. AP-1 induces expression of certain MMPs. The agents that prevent photoaging can act on the MMPs, the transcription factors AP-1 and NF-κB, and/or one or more of the molecules involved in the three kinase cascades shown in FIG. 1. Aspirin and E5510 (described by Fujimori, T., et al., Jpn J Pharmacol (1991) 55(1):81–91) inhibit NF-κB activation. Farnesyl transferase inhibitors such as B-581 (described by Garcia A. M., et al., J Biol Chem (1993) 268(25):18415–18), BZA-5B (described by Dalton M. B. et al., Cancer Res (1995)55(15):3295–3304), farnesyl acetate, and (α-hydroxyfarnesyl) phosphoric acid act on RAS and inhibit activation of the ERK cascade; whereas geranyl geranyltransferase inhibitors and lisofylline inhibit activation of the JNK cascade. Compounds such as SB202190 (described by Lee, J. C., et al., Nature (1994) 372:739–746) and PD98059 (described by Dudley, D. T., et al., PNAS (USA) (1995) 92:7686–7689) inhibit specific kinases in the cascades. Retinoids such as those disclosed in U.S. Pat. No. 4,877,805 and the dissociating retinoids that are specific for AP-1 antagonism such as those described by Fanjul, et al., Nature (1994) 372:104–110, glucocorticoids, and Vitamin D3 target AP-1. Finally, MMPs may be inhibited by BB2284 (described by Gearing, A. J. H. et al., Nature (1994) 370:555–557), GI129471 (described by McGeehan G. M., et al., Nature (1994) 370:558–561), TIMPs, Galardin, Batimastat and Marimastat and hydroxamates, and other known inhibitors.

One or more of these MMP inhibitors are preferably administered topically to the skin that is to be exposed to sunlight. For such administration they will normally be formulated as creams, gels, ointments, sprays or lotions. Conventional pharmacologically and cosmetically acceptable vehicles may be used to formulate the inhibitor(s). Examples of such vehicles are described in U.S. Pat. No. 4,877,805 and EPA Pub. No. 0586106A1. As indicated one or more inhibitors may be present in a given formulation. For instance, a combination of inhibitors that act on two or more different molecules involved in effecting MMP degradation of the skin may be used. The formulations may also contain additives such as emollients, skin permeation enhancers, pigments, and perfumes. In addition, the formulation may contain ingredients such as absorbent particles (e.g. polymer beads) that provide sustained release of the inhibitors to the skin. The weight concentration of inhibitor(s) in the formulation will usually be 0.01% to 10%, more usually 0.1% to 1%. Normally about 50 mg of formulation will be applied per cm² of skin.

The inhibitors are preferably applied to the undamaged skin prior to exposure to sunlight. The application regimen (i.e. daily, weekly, etc.) will primarily depend upon the longevity (e.g. metabolism, half-life in the skin) of the inhibitor(s) and the molecular targets of their action. It may also be effected by bathing, perspiration, and the extent of sunlight exposure. Usually they will be applied daily.

The invention is further illustrated by the following examples. These examples are not intended to limit the invention in any manner.

EXAMPLES

Determination of Molecular Basis of UVB-Induced Photoaging

High UVB Dose Induction of MMPs

The time course of changes in MMP-1, MMP-3, MMP-9, and MMP-2 mRNA, protein, and enzymatic activity levels following UVB exposure were determined as follows.

Subjects were adult Caucasians (approximately equal numbers of males and females) with light to mild pigmentation. The UVB dose required to cause barely perceptible skin reddening (minimal erythema dose, MED) for each subject was determined 24 hours post irradiation. 1MED for all subjects ranged from 30–50 mJ/cm². The subjects' buttocks were irradiated with 2MED UVB with an Ultralite Panelite lamp containing four F36T12 ERE-VHO UVB tubes. Irradiation intensity was monitored with an IL443 Phototherapy Radiometer and a SED240/UVB/W photodetector. UVB output, measured 48 cm from the source, was 0.5 mW/cm². For each subject skin was removed by keratome from four sites (one non-irradiated, three irradiated) at 8, 16, 24, 48 and 72 hours following irradiation. Tissue was snap frozen and total RNA isolated and analyzed by Northern blot as described by Fisher, G. J. et al., J Invest Dermatol (1991) 96:699–707. Band intensities were quantified by PhosphorImager. Values for MMP transcripts were normalized to those for control gene 36B4. The results of these tests are shown in FIGS. 2a (MMP-1), 2b (MMP-3), 2c (MMP-9), and 2d (MMP2). Results are means±SEM (n=6 for 8, 16, 48, and 72 hours and n=17 for no UVB control and 24 hours) and are presented as fold increase of normalized values relative to non-irradiated skin. The bands displayed in the Figures are composites from several individuals.

As shown in FIGS. 2a–d induction of MMP-1, MMP-3, and MMP-9 mRNAs was maximal (6–60 fold) within 16 to 24 hours and returned to near baseline within 48 to 72 hours. MMP-2 mRNA was detectable, but only elevated 1.6-fold 24 hours post irradiation. Time courses for induction of MMP-1 and MMP-9 proteins and activities by 2MED UVB paralleled those observed for their mRNAs. Neither MMP-2 protein nor activity was induced.

Northern analysis of UVB-treated skin with a MMP-3 (stromelysin I)-specific probe yielded results identical to those obtained with a full-length MMP-3 probe (FIG. 2b), while hybridization with a MMP-10 (stromelysin II)-specific probe yielded no signal. This indicates that among the stromelysins, UVB induces predominantly stromelysin 1.

Low Dose UVB Induction of MMPs

Subjects were exposed to UVB doses ranging from 0.01 to 2MED as described above. Full thickness skin samples (6mm cylinders) were obtained 24 hours after irradiation from treated and untreated sites. The samples were homogenized in 20 mM Tris HCl (pH 7.6), 5 mM $CaCl_2$, and centrifuged at 3000×g for 10 minutes. Supernatants were used to measure MMP-1 and MMP-9 proteins by Western blot (100 μg/lane), using chemiluminescence detection and activity by hydrolysis of $^3H$ fibrillar collagen (100 μg/assay) according to Hu, C. L. et al., Anal Biochem (1978) 88:638–643 and gelatin zymography (20 μg/assay) according to Hibbs, M. S. et al., J Biol Chem (1985) 260:2493–2500, respectively. The MMP-2 and MMP-9 antibodies used are described by Werb, Z. et al., J Cell Biol (1989) 109:877–889 and Murphy, G. et al., Biochem J (1989) 258:463–472, respectively. The results of these tests are shown in FIGS. 3a and 3b.

Figure 3A:
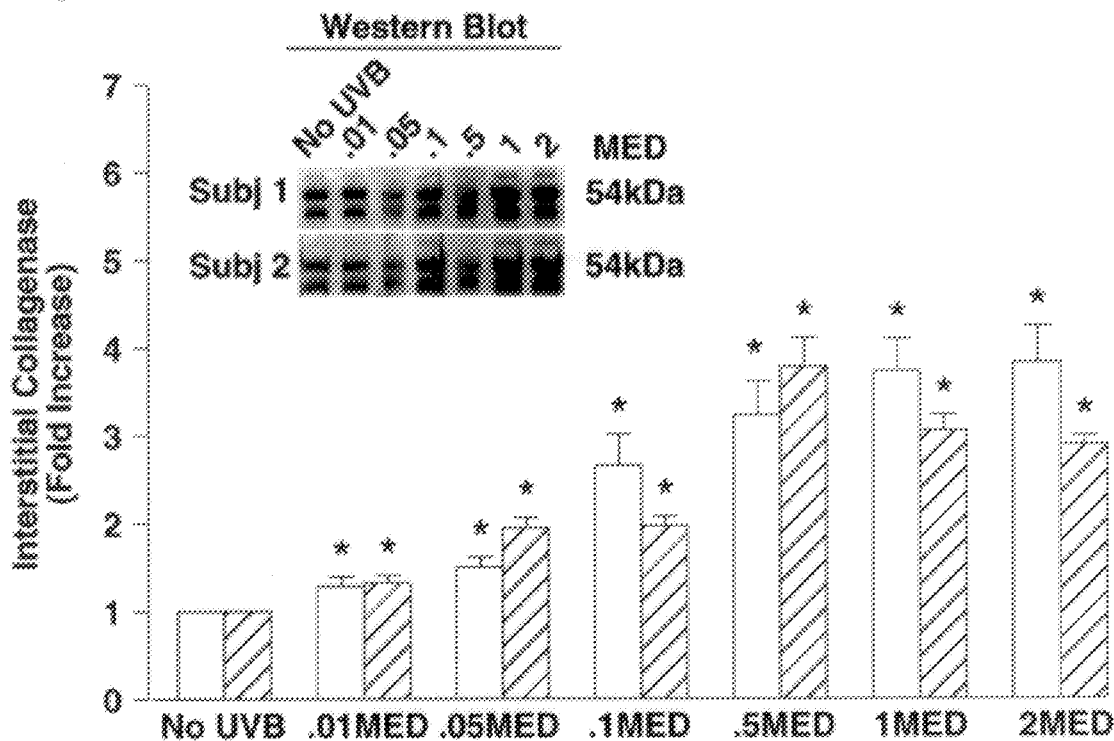

In FIG. 3a MMP-2 protein values are shown by the open bars whereas MMP-2 activity values are shown by the cross-hatched bars. The FIG. 3a inset shows representative Western blots from two subjects. The larger 54 KDa band is intact MMP-2 and the smaller 45 KDa band is the proteolytically processed activated form of MMP-2.

Figure 3B:
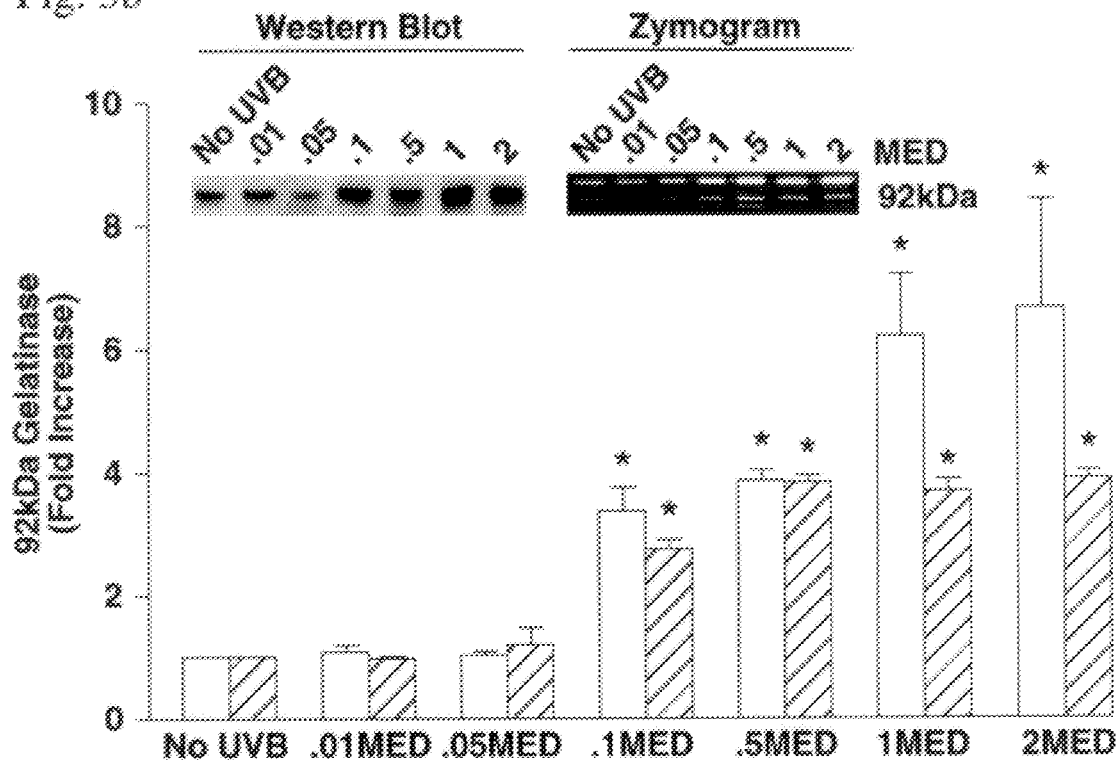

In FIG. 3b MMP-9 protein values are shown by the open bars where MMP-9 activity values are shown by the cross-hatched bars. The FIG. 3b inset shows a representative Western blot (left panel) and a representative zymogram (right panel). Multiple bands on the zymogram are proteolytically processed active forms of MMP-9.

Band intensities were quantified by laser densitometry. Results are given as means±SEM of n=10.

As shown in FIGS. 3a and 3b induction of MMP-2 and MMP-9 proteins and activities was dose dependent, and for both MMPs changes in protein and activity mirrored each other. MMP-2 was induced by all doses of UVB tested, while MMP-9 was induced by doses ≧0.1 MED. Induction was maximal at 1MED and approximately half maximal at 0.1 MED. 0.1 MED UVB is equivalent to two to three minutes solar irradiation on a summer day, which causes no perceptible skin reddening.

Low Dose UVB Induction of AP-1 and NF-κB

Subjects were irradiated and tissue samples taken as described above. Nuclear extracts were prepared from the samples as described by Fisher, G. J. et al., J Biol Chem (1994) 269:20629–20635. Biopsies (approx. 200 mg wet weight) containing~$10^8$ cells yielded 500 μg nuclear extract protein, on average. Electrophoretic mobility shift assays (8 μg nuclear extract protein) were performed using $^{32}P$-labeled DNA probes containing AP-1 and NF-κB consensus and mutated DNA-binding sequences as described by Fisher, G. J. et al., supra. Antibodies for supershifts were obtained from Santa Cruz Biotechnology. Jun and fos antibodies had broad reactivity to all jun and fos family members, respectively. NF-κB antibody was specific for p65/Rel A. The results of these assays are shown in FIGS. 4a, 4b, 4c and 4d (NS designates non-specific examples). The insets for these Figs. show representative AP-1 and NF-κB retarded complexes. +Compet designates addition of 100-fold excess unlabelled probe; Mut designates mutated $^{32}p$ probe.

Figure 4A:
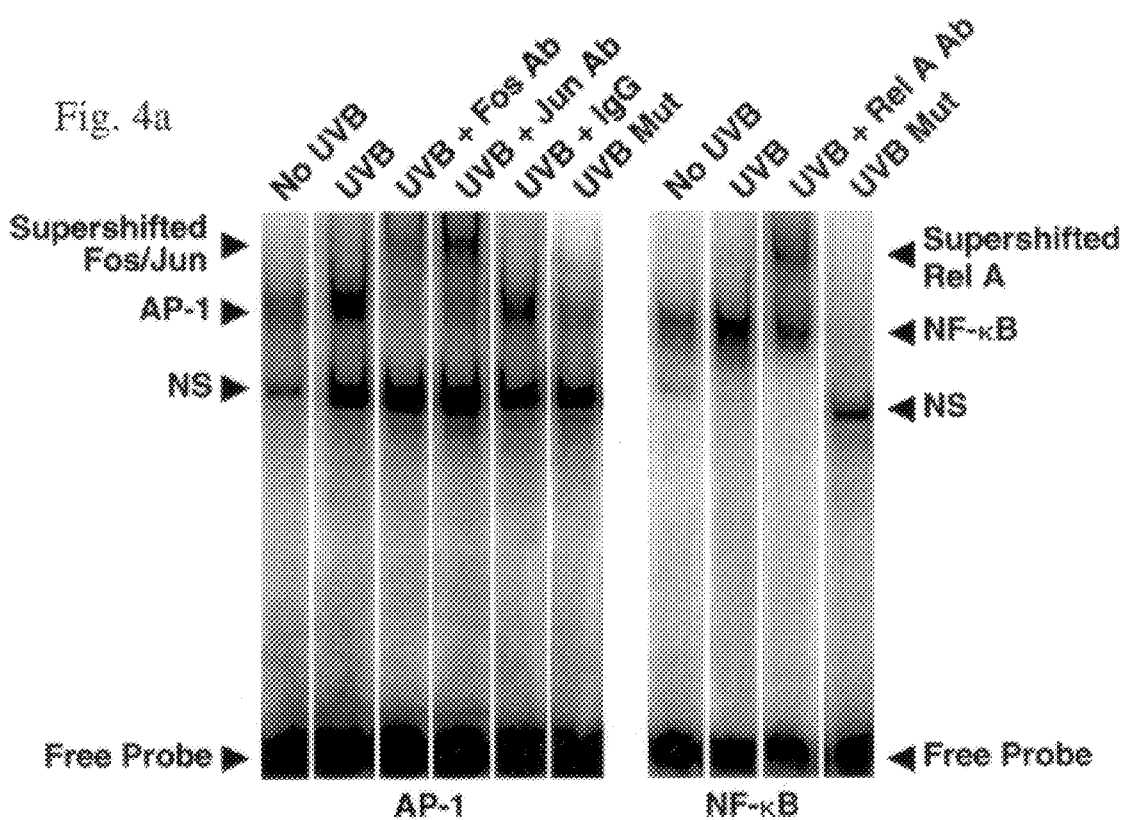

FIG. 4a depicts AP-1 and NF-κB binding in non-irradiated and irradiated (four hours after 2MED UVB) skin. As shown in FIG. 4a binding of both transcription factors to their DNA response elements was specific as demonstrated by loss of retarded complexes with mutated labeled probes. Antibody supershifts demonstrated that the specific AP-1 and NF-κB retarded complexes observed with extract from UVB-irradiated skin contained jun and fos proteins, and Rel A protein, respectively.

Figure 4B:
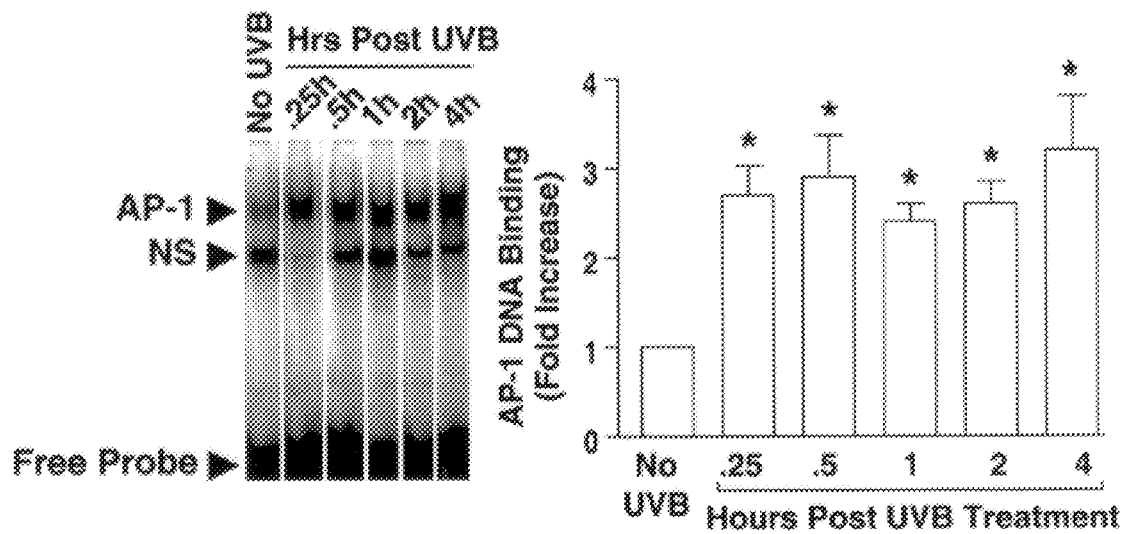

FIGS. 4b and 4c show the time courses of induction of AP-1 and NF-κB DNA binding, respectively, by 2MED UVB. The results reported are means±SEM, n=9. As shown induction of both factors occurred within 15 minutes.

FIG. 4d shows the dose dependence of induction of AP-1 (represented by open bars) and NF-κB (represented by cross-hatched bars). DNA binding was measured 30 minutes after irradiation. As shown half maximal induction of both factors occurred at approximately 0.1 MED and maximal induction occurred at 1MED. The UVB dose dependencies for induction of these factors closely matched those reported above for induction of MMP-2 and MMP-9, consistent with the participation of these transcription factors in the UVB-induced increases in these two MMPs.

Inhibition of UVB Induction of AP-1, MMP-2 and MMP-9

0.1% all-trans retinoic acid (t-RA) and its vehicle (70% ethanol and 30% propylene glycol) or 0.05% of the glucocorticoid (GC) clobetasol propionate and its vehicle (2% propylene glycol, 2% sorbitan sesquioleate in white petrolatum) were applied (300 mg formulation/6cm$^2$ skin) to subjects for 48 hours as described by Fisher, G. J. et al., J Invest Dermatol (1991) 96:699–707. Treated skin sites were then irradiated with 2MED UVB. Skin was obtained as described above 30 minutes after exposure to AP-1 measurements or 24 hours after exposure for MMP measurements. AP-1 measurements and MMP-1 and MMP-9 measurements were made as described above. To determine whether t-RA altered UVB-induced skin reddening, subjects were treated with 0.1% t-RA and its vehicle for 24 hours. Treated areas were irradiated with 10–80 mJ/cm$^2$ UVB and skin reddening determined 24 hours after by a Minolta chromameter. The results of these tests are shown in FIGS. 5a, 5b, 5c, 5d and 5e.

FIGS. 5a reports the AP-1 measurements. As shown pretreatment of skin with t-RA reduced UVB-induced AP-1 DNA binding by approximately 70%.

Figure 5B:
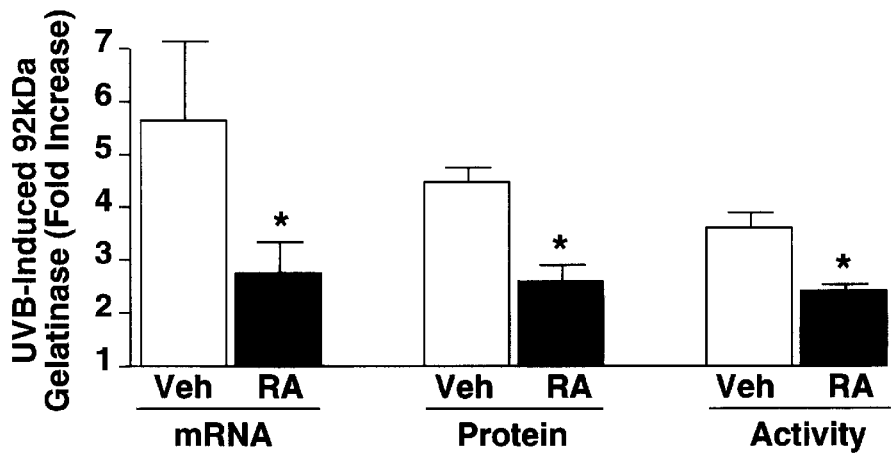
Figure 5C:
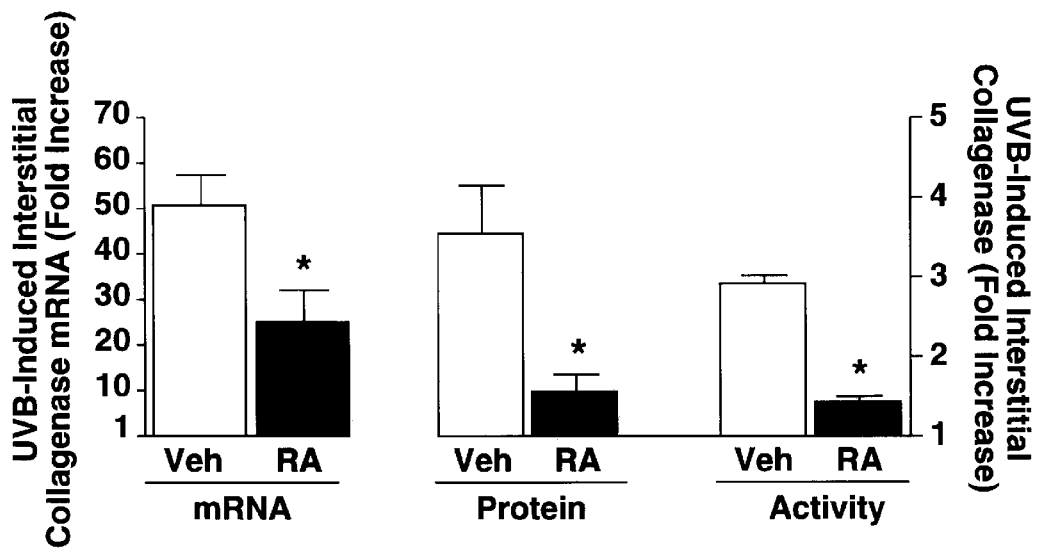

FIGS. 5b and 5c report the MMP-1 and MMP-9 measurements. As shown, t-RA pretreatment reduced UVB-induced MMP-1 and MMP-9 mRNAs, proteins and activities 50%–80%.

Figure 5D:
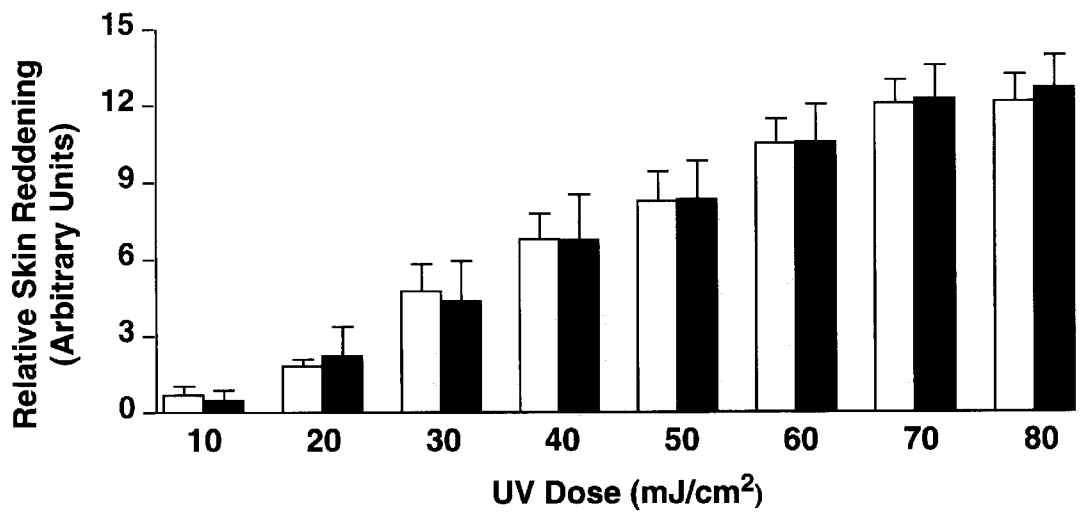

FIG. 5d reports that the tests on the effect of t-RA pretreatment on skin reddening. As shown, although t-RA absorption overlaps the UVB range (t-RA λmax=351 nm)

t-RA did not reduce UVB-induced skin reddening. This indicates that the observed reductions in AP-1 and MMP induction were specific rather than due to absorption of UVB by t-RA.

Figure 5E:
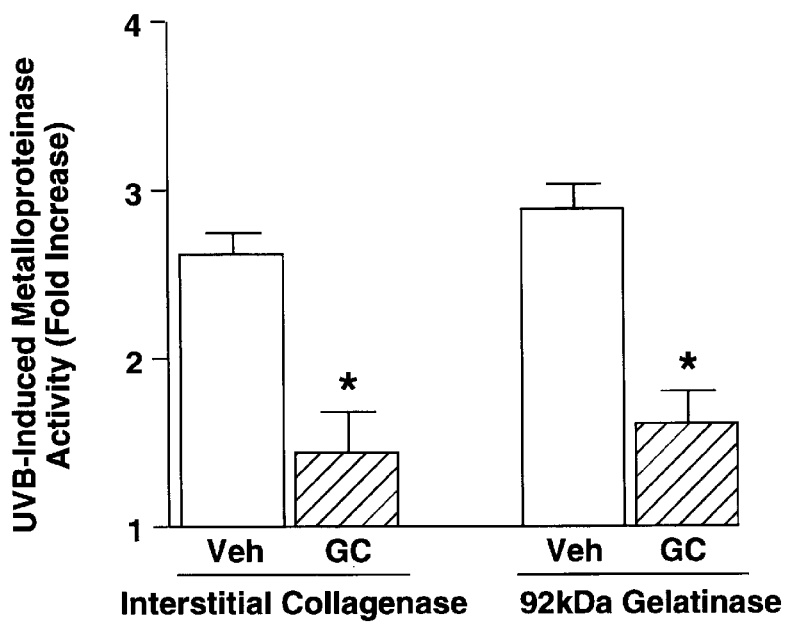

FIG. 5e reports the effects of pretreatment of the skin with GC. As shown GC pretreatment reduced MMP-1 and MMP-9 activities to extents similar to those observed from t-RA pretreatments.

The publications referred to in the above specification are hereby expressly incorporated by reference.

We claim:

1. A method for inhibiting photoaging of unphotodamaged skin of a human due to exposure of the skin of the human to ultraviolet B radiation (UVB) comprising administering an inhibitor of a UVB-inducible matrix metalloproteinase (MMP) to the human prior to said exposure in an amount sufficient to inhibit the production or activity of UVB-inducible MMPs in said skin.

2. The method of claim 1 wherein said exposure provides a dose of UVB below the minimum dose required to cause reddening of said skin.

3. The method of claim 2 wherein said dose is above about 5 mJ/cm$^2$.

4. The method of claim 1 wherein the inhibitor inhibits the activity of at least one of AP-1 and NF-κB.

5. The method of claim 1 wherein the inhibitor inhibits the activity of UVB-inducible MMPs.

6. The method of claim 1 wherein the inhibitor inhibits a GTP binding protein or kinase essential to the production of jun or fos proteins.

7. The method of claim 4 wherein the inhibitor inhibits AP-1 and is a retinoid, a glucocorticoid, or Vitamin D3.

8. The method of claim 4 wherein the inhibitor inhibits NF-κB and is a glucocorticoid, aspirin or E5510.

9. The method of claim 5 wherein the inhibitor is a TIMP, Galardin, Batimastat, Marimastat, or a hydroxamate.

10. The method of claim 6 wherein the inhibitor is a farnesyl transferase inhibitor, a geranyl geranyltransferase inhibitor, SB202190, or PD98059.

11. In the process of manufacturing a medicament for topical administration to the skin before exposure to sunlight to ameliorate the effects of sunlight on human skin, which process includes combining at least one active ingredient and a dermatologically suitable carrier therefor, the improvement comprising the use of an inhibitor of an ultraviolet B radiation-inducible matrix metalloproteinase as an active ingredient.

12. The method of claim 1, wherein said exposure to UVB is caused by exposure to sunlight.

13. The method of claim 2, wherein said exposure to UVB is caused by exposure to sunlight.

14. The method of claim 11, wherein said active ingredient inhibits photoaging induced by exposure to solar UVB below the minimum dose required to cause reddening of said skin.

15. The method of claim 14, wherein the active ingredient is a retinoid.

16. The method of claim 11, wherein the inhibitor inhibits the activity of at least one of AP-1 and NF-κB.

17. The method of claim 11, wherein the inhibitor inhibits the activity of UVB-inducible MMPs.

18. The method of claim 11, wherein the inhibitor inhibits a GTP binding protein or kinase essential to the production of jun or fos proteins.

19. The method of claim 11, wherein the inhibitor inhibits AP-1 and is a retinoid, a glucocorticoid, or Vitamin D3.

20. The method of claim 11, wherein the inhibitor is a farnesyl transferase inhibitor, a geranyl geranyltransferase inhibitor, SB202190, or PD98059.

* * * * *

UNITED STATES PATENT AND TRADEMARK OFFICE
CERTIFICATE OF CORRECTION

PATENT NO. : 5,837,224

DATED : November 17, 1998

INVENTOR(S) : John J. Voorhees and Gary J. Fisher

It is certified that error appears in the above-indentified patent and that said Letters Patent is hereby corrected as shown below:

Column 5, line 35, change "MMP-2" to --MMP-1--;
          line 40, change "MMP-2" to --MMP-1--;
          line 41, change "MMP-2" to --MMP-1--;
          line 45, change "MMP-2" to --MMP-1--;
          line 54, change "MMP-2" to --MMP-1--;
          line 57, change "MMP-2" to --MMP-1--;

Column 6, line 36, change "MMP-2" to --MMP-1--;
          line 39, change "MMP-2" to --MMP-1--;

Signed and Sealed this

Tenth Day of April, 2001

Attest:

NICHOLAS P. GODICI

Attesting Officer      Acting Director of the United States Patent and Trademark Office